United States Patent [19]

Jones, Jr.

[11] Patent Number: 4,504,687

[45] Date of Patent: Mar. 12, 1985

[54] METHOD FOR ETHERIFICATIONS

[75] Inventor: Edward M. Jones, Jr., Friendswood, Tex.

[73] Assignee: Chemical Research & Licensing Company, South Houston, Tex.

[21] Appl. No.: 529,926

[22] Filed: Sep. 7, 1983

Related U.S. Application Data

[63] Continuation of Ser. No. 349,043, Feb. 16, 1982, abandoned.

[51] Int. Cl.$^3$ .............................................. C07C 41/05
[52] U.S. Cl. .............................. 568/697; 203/DIG. 6
[58] Field of Search .................. 568/697; 203/DIG. 6

[56] References Cited

U.S. PATENT DOCUMENTS

| | | |
|---|---|---|
| 2,081,322 | 5/1937 | Carney . |
| 2,707,165 | 4/1955 | McLean et al. . |
| 3,241,926 | 3/1966 | Parker et al. . |
| 4,232,177 | 11/1980 | Smith . |
| 4,307,254 | 12/1981 | Smith . |
| 4,336,407 | 6/1982 | Smith . |

*Primary Examiner*—Howard T. Mars
*Attorney, Agent, or Firm*—Kenneth H. Johnson

[57] ABSTRACT

A method for producing tertiary ethers from $C_4$ or $C_5$ streams containing isobutene and isoamylene respectively in a process wherein a acidic cation exchange resin is used as the catalyst and as a distillation structure in a distillation reactor column, wherein the improvement is the operation of the catalytic distillation in two zones at different pressures, the first zone containing the catalyst packing and operated a higher pressure in the range of 100 to 200 psig in the case of $C_4$'s and 15 to 100 psig in the case of $C_5$'s which favors the etherification reaction and the second zone being a distillation operated at a lower pressure in the range of 0 to 100 psig in the case of $C_4$'s and 0 to 15 psig in the case of $C_5$'s wherein a first overhead from the first zone is fractionated to remove a portion of the unreacted alcohol from the first overhead and to return a condensed portion containing said alcohol to the first zone and to produce a second overhead having less alcohol than said first overhead.

13 Claims, 3 Drawing Figures

METHOD FOR ETHERIFICATIONS

The Government of the United States of America has certain rights in this invention pursuant to Contract No. DE-FC07-80CS40454 awarded by the U.S. Department of Energy.

This application is a continuation of application Ser. No. 349,043, filed 2/16/82, now abandoned.

BACKGROUND OF THE INVENTION

Field of the Invention

The present invention relates to a method for conducting etherification of $C_4$ and $C_5$ tertiary olefins in $C_4$ and $C_5$ refinery streams with lower alcohols in concurrent etherification-distillation reactors to reduce azeotroped alcohol in the unreacted $C_4$ and $C_5$ distillate from the reactors.

Related Art

The process of concurrent reaction and distillation of the reaction component using the reaction catalyst as the distillation component is known as catalytic distillation and is described along with suitable catalyst structures in several commonly assigned U.S. patents and applications, including U.S. Pat. Nos. 4,215,011; 4,232,177; 4,242,530; 4,250,052; 4,302,356; 4,307,254 and Ser. No. 234,653 filed Feb. 17, 1981.

Among the attributes of this process are:

(1) The utilization of a single reactor for carrying out the reaction and the initial distillion of the reaction mixture. Thus, initial investment in new equipment is substantially lower than liquid phase reactors and separate distillation towers. However, this aspect of the catalytic distillation gives rise to a further capital investment advantage in that the system can be retrofitted into existing distillation towers at a substantial savings in cost and time. This is an important consideration, since most refineries have unused or expendable distillation towers adequately suited for retrofitting.

(2) The catalytic reaction is very likely exothermic such as the etherifications and in those reactions where it is, the heat of reaction is used for the distillation (and supplemented by added heat as necessary).

(3) In exothermic reactions, such as etherifications, the heat of reaction has been a problem, since in conventional reactions the heat must be dispersed or the reaction becomes a runaway, produces undesired by-products or certain types of catalyst can be damaged. In the catalytic distillation, excess heat merely causes more boil-up and hence by controlling the pressure the temperature in the reactor is controlled and the heat of reaction is utilized as desired. Thus, in commercial scale the present process has proven very easy to start up, control and shut down. In other words, the reaction system has the ease and simplicity of operation of a distillation.

The U.S. Department of Energy has supported the development of the catalytic distillation system and the process utilization thereof because of its potential to conserve energy, in particular, the commercial use of this process for producing ethers utilizing methanol as a reactant to thereby incorporate significant amounts of methanol into the nations gasoline supply, thus decreasing dependence on oil.

The first ether approved as an octane improver for gasoline is methyl tertiary butyl ether (MTBE). The ethers have very high blending octane numbers and may be blended into gasoline in significant amounts.

The first commercial catalytic distillation plant was placed on stream at Charter International Oil Company's Houston Refinery for producing MTBE and/or oligomers of isobutene in 1981. This demonstration plant established the viability of this totally new process technology and the attributes thereof.

In the manufacture of MTBE by the catalytic distillation process, it is preferable to conduct both the reaction of methanol with isobutene in the $C_4$ refinery stream and the methanol-MTBE separation distillation at a relatively high pressure, e.g., 150 psig, to obtain high reaction rate and to expedite the azeotropic removal of methanol from the MTBE product. It should be appreciated that the MTBE added to gasoline must be substantially free of methanol, since methanol will phase out in any water in the storage tanks and result in a change in octane number and a loss of methanol.

The $C_4$ refinery streams normally contain 9 to 60 weight percent isobutene with the major portion of these streams containing less than 20 weight percent isobutene. The remainder of the stream is n-butene, isobutane and n-butane with small amounts of $C_3$'s and $C_5$'s. The isobutene is preferentially reacted with the methanol. A full description of the etherification is found in commonly assigned U.S. Pat. No. 4,307,254 and U.S. patent application Ser. No. 234,653, filed Feb. 17, 1981 both of which are incorporated herein in their entirety.

At the high pressures normally employed in the process the composition of the overhead from the catalytic distillation reactor is unreacted isobutene, the remainder of the $C_4$ stream and 6.0–6.5 weight percent methanol. This methanol contributes significantly to the total heat input to the reactor, and its subsequent recovery by water extraction and distillation is also a significant energy requirement. It is known that the composition of the methanol-mixed $C_4$ azeotrope is considerably lower in methanol at lower pressures, being about 3 weight percent at 70 psig and nearly zero at atmospheric pressure. Similarly, it is known that the composition of the methanol-fixed $C_5$ azeotrope is considerably lower in methanol at lower pressures. Because of the higher boiling points of the $C_5$'s, however, the reactions and distillations of $C_5$ compounds are generally carried out at lower pressure than are the analogous $C_4$ procedures. Thus, it becomes advantageous to operate the reaction column at as low a pressure as possible to minimize the energy required to distill the overhead product, and thereby also minimize the energy requirement for recovery of the methanol. Hence the operation of the reaction and the distillation are to some extent in opposition to each other.

It is an advantage of the present invention to provide optimum conditions of operation for both the reaction and distillation. It is a further advantage that less heat is required to operate the catalytic distillation according to the present invention. It is further advantage that less alcohol is carried out of the reactor and less energy is required in the recovery of the alcohol.

SUMMARY OF THE INVENTION

Briefly, the present invention is a method for producing $C_1$ or $C_2$ alkyl tertiary $C_4$ or $C_5$ ether comprising:
(a) feeding:
 (1) a $C_4$ or $C_5$ hydrocarbon stream containing isobutene or isoamylene, respectively, and (2) an alcohol selected from methanol or ethanol, to a first zone of a distillation column reactor, having two zones operated at different pressures, said first zone containing a fixed bed acidic cation exchange resin, (b) concurrently:
(1) contacting said $C_4$ or $C_5$ hydrocarbon stream and said alcohol with said fixed bed acidic cation exchange resin packing in said first zone at a pressure in the range of 100 to 200 psig in the case of $C_4$'s, or 15 to 100 psig in the case of $C_5$'s, thereby catalytically reacting isobutene or isoamylene with said alcohol to form $C_1$ to $C_2$ tertiary $C_4$ or $C_5$ ether;
(2) distilling the resulting mixture comprising said ether and unreacted materials in said first zone,
(3) removing from said first zone a first overhead fraction comprising principally unreacted $C_4$ or $C_5$ hydrocarbons and containing minor amounts of ether and alcohol as an azeotrope into a second zone, said second zone being a distillation zone operated at a pressure in the range of 0 to 100 psig in the case of $C_4$'s, or 0 to 15 psig in the case of $C_5$'s, thereby producing a second overhead having a reduced amount of alcohol therein from said first overhead, condensing a portion of said first overhead, said condensed portion containing substantially all of said ether and a portion of said alcohol of said first overhead and returning said condensed portion to said first zone,
(4) withdrawing said second overhead from said second zone and
(5) withdrawing an ether product substantially free of alcohol from the bottom of said first zone.

An additional step is the condensation of the second overhead and removal of alcohol therefrom.

In another embodiment the feed is a mixed $C_4$ and $C_5$ hydrocarbon stream containing at least one of isobutene or isoamylene, to produce a mixed ether product.

The alcohol, methanol or ethanol, has a higher heat of vaporization than the $C_4$ or $C_5$; thus, removing the alcohol from the overhead and returning it to the catalyst section reduces the energy needed to perform the necessary distillation in the distillation reactor column. A second energy savings occurs downstream of the column, since less alcohol is carried overhead out of the column to the alcohol recovery section. It should be appreciated that the alcohol recovery is essential for two reasons. First, in a large scale commercial operation, the amount of alcohol azeotroped with the unreacted $C_4$ and $C_5$ stream components is substantial and must be returned to the reactor or otherwise used for process economics. Secondly the $C_4$ and $C_5$ overheads are hydrocarbon streams, destined for utilizations where the alcohol may be an undesirable impurity; thus, at some point the alcohol must be removed therefrom.

As described earlier the present catalytic distillation process can be readily retrofitted into existing distillation towers. However, it should be appreciated that the two zones need not be physically in the first tower, since the first zone can be in a first column with the overhead therefrom being fed to the bottom of a second column. Hence, the present invention actually provides the catalytic distillation process with greater flexibility since two small towers can be used to obtain the improved result.

The effect of pressure on the azeotropes of the alcohols and the $C_4$ and $C_5$ streams is known and may be determined by simple experimentation of the particular (i.e., typical) feed for specific column or estimated by empirical methods.

The pressure in each zone in the broadest embodiment of the present invention would appear to overlap at 100 psig in the case of $C_4$'s, or at 15 psig in the case of $C_5$'s; however, that pressure represents two extremes of the ranges and the column would not be operated at the same or substantially the same pressure in both sections since there would be no advantage to having two zones. The upper distillation zone could be operated at 100 psig in the case of $C_4$'s or at 15 psig in the case of $C_5$'s if certain conditions exist downstream, such as air cooling of the overhead. Similarly, the catalyst distillation section could be operated at 100 psig in the case of $C_4$'s or 15 psig in the case of $C_5$'s at very low rates of conversion. It is expected, however, in the case of $C_4$'s the upper (distillation) section or zone of the column would preferably be operated at 65 to 85 psig and more preferably 70–75 psig and the lower (catalyst distillation) section or zone would preferably be operated at 140 to 185 psig and more preferably 150 to 180 psig. In the case of $C_5$'s, the upper (distillation) section or zone would preferably be operated at 5 to 15 psig, more preferably 10 to 15 psig, and the lower (catalyst distillation) section would preferably be operated at 15 to 80 psig, more preferably 30 to 70 psig. In the case of a mixed $C_4$–$C_5$ feed, the operating pressures are selected to give the corresponding temperatures, depending on the liquid composition present. Preferably the pressure in the upper distillation zone is less than the pressure in the catalytic zone.

DETAILED DESCRIPTION OF THE INVENTION AND SPECIFIC EMBODIMENTS

Figure 1:
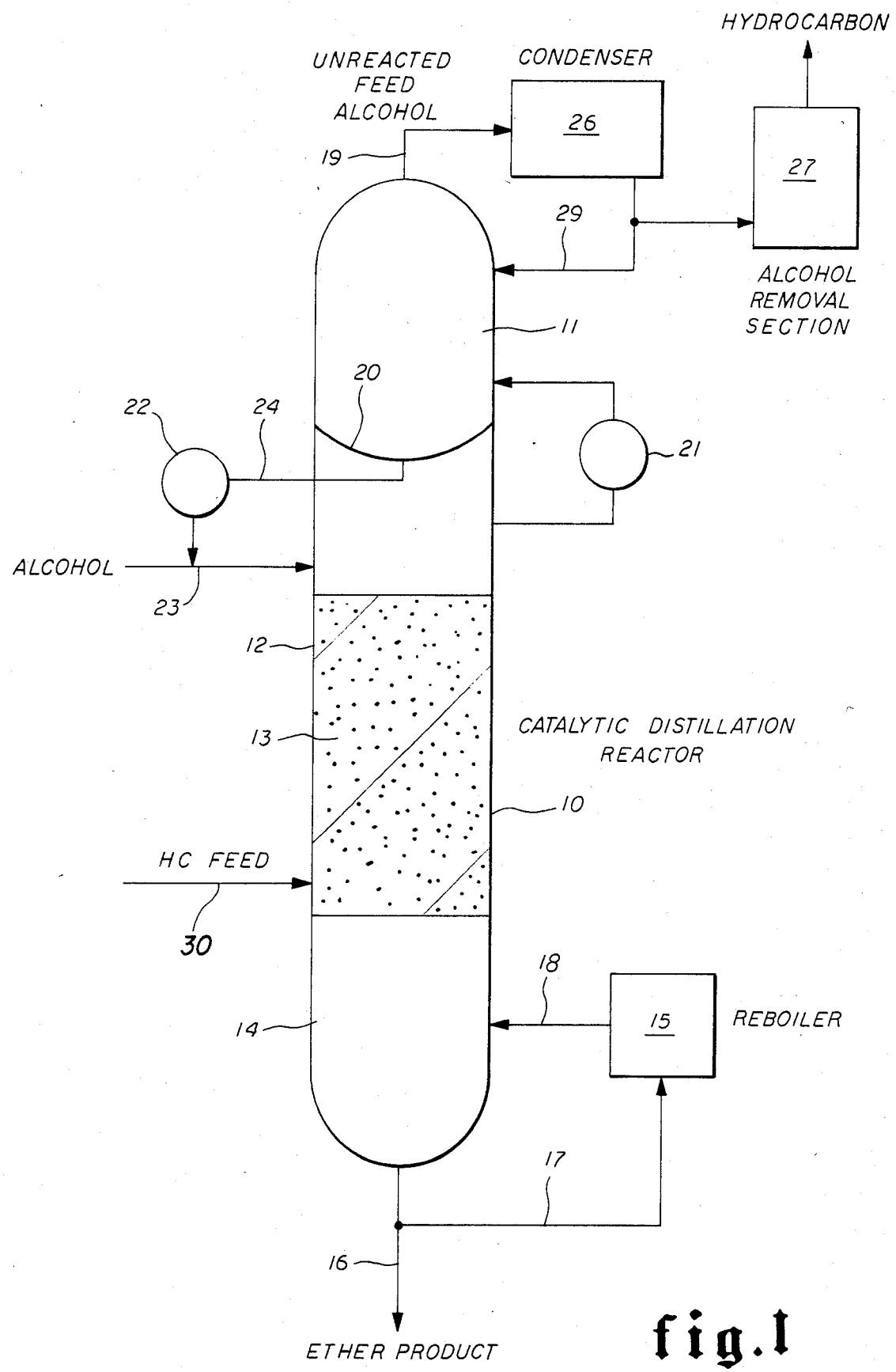
FIG. 1 is a schematic representation of a two pressure stage etherification.

The term "catalyst" or "catalytic material" is used to include any solid material which is recognized for the reaction under consideration as performing as a catalyst therein. Furthermore, the catalytic material must be in a form to serve as a distillation packing, for example, rings, saddles, balls, irregular pieces, sheets, tubes, spirals, packed in bags (as described in U.S. Pat. No. 4,242,530), plated on grills or screens, or reticulated polymer foams (the cellular structure of the foams must be sufficiently large so as not to cause high pressure drops through the columns or otherwise arranged, such as in chunks or concentric tubes to allow vapor flow). Broadly stated, the catalytic material is a component of a distillation system functioning as both a catalyst and distillation packing, i.e., a packing for a distillation column having both a distillation function and a catalytic function.

The iso $C_4$ and iso $C_5$ olefins are more reactive than the corresponding normal olefins and can be removed in substantially quantitative amounts from $C_4$ and $C_5$ streams in which they are components. The $C_4$ and $C_5$ olefins may be in a single stream; however, normally these streams are separated and the stream to be contacted wit the alcohol is substantially a $C_4$ or $C_5$ stream containing only minor amounts of other hydrocarbons.

The greater reactivity of the isoolefins compared to the corresponding normal olefins, provides an excellent means of separating the two by formation of the isoethers and concurrent fractionation (distillation) of the resulting product stream according to the present invention whereby the unreacted normal olefin is removed as an overhead and the ether product is removed as a bottom.

The manner of operating the catalytic zone of the distillation column reactor, i.e., the severity of the conditions, is easily determinable by the operator to obtain the desired result, i.e., to react substantially only the isoolefin with the alcohol and to separate the isoolefin ether and recover the normal olefin within the ranges of pressure taught.

The ether products in the case of isobutene are tertiary butyl alkyl ether and isobutyl alkyl ether and similarly the products in the case of isoamylene are tertiary amyl alkyl ether and isoamyl alkyl ethers.

Preferably the feed to distillation reactor is either a substantially $C_4$ or $C_5$ stream. There may be a mixture of olefins, i.e., iso and normal as well as the corresponding alkanes. The reaction can be carried out with only the isoolefin; however in such a case there would normally be a small amount, e.g., 0.5 to 15 mole % up to 25 or 30 mole % of a non reactive diluent present such as a normal alkane which has a lower boiling point than the ether product for control of the reaction. Since the alcohol is present, side reactions such as oligomerization of the olefins would be suppressed.

One species of the present invention is a method for the preparation of methyl tertiary butyl ether from streams containing mixtures of isobutene and normal butenes.

Other species include the production of ethyl tertiary butyl ether, methyl tertiary amyl ether, and ethyl tertiary amyl ether.

Another species of the present invention is the separation of the isoolefins from the corresponding normal olefins, since these are not separable by distillation.

The reaction system can be described as heterogeneous since the catalyst remains as a distinct entity. The catalyst may be employed in such conventional distillation packing shapes as Raschig rings, Pall rings, saddles or the like. Similarly, the resin may be employed in a granular or bead form as described herein and the noted patents.

The alcohol, i.e., methanol or ethanol may be and is preferably present in at least a stoichiometric amount although an excess is desirable. In addition, slightly less than a stoichiometric amount may be employed. It should be appreciated that the skilled chemist will optimize the proportions and precise conditions for each particular piece of equipment and variation in catalyst, once the basic invention is comprehended.

It has been found that the resin beads in a conventional fixed bed form too compact a mass for the upward flowing vapor and downward flowing liquid. However, it has been found that placing the resin beads into a plurality of pockets in a cloth belt, which is supported in the distillation column reactor by open mesh knitted stainless steel wire by twisting the two together, allows the requisite flows, prevents loss of catalyst, allows for the normal swelling of the beads and prevents the breakage of the beads through mechanical attrition. This novel catalyst arrangement is described in detail in commonly owned U.S. Pat. No. 4,242,530, which is incorporated herein.

The cloth may be of any material which is not attacked by the hydrocarbon feed or products or catalyst under the conditions of the reaction. Cotton or linen may be useful, but fiber glass cloth or "Teflon" cloth are preferred. Briefly, a preferred catalyst system comprises a plurality of closed cloth pockets arranged and supported in said distillation column reactor by wire mesh intimately associated therewith.

The particular catalytic material may be a powder, small irregular fragments or chunks, small beads and the like. The particular form of the catalytic material in the cloth pockets is not critical, so long as sufficient surface area is provided to allow a reasonable reaction rate. This sizing of catalyst particles can be best determined for each catalytic material (since the porosity or available internal surface area will vary for different materials and of course affects the activity of the catalytic material).

What readily distinguishes the present method from the prior art is that the prior art has consistently employed a continuous liquid phase system for contacting the isoolefin with the acidic catalyst, whereas the present invention carries out the method in a catalyst packed distillation column which can be appreciated to contain a vapor phase and some liquid phase as in any distillation.

The etherification reaction, e.g., of isobutene, and the fractionation of the resultant n-butene-ether mixture is carried out simultaneously, i.e., concurrently. That is, as the ether is formed in the catalyst bed, the lower boiling n-butene is fractionated away in the catalyst bed and removed overhead while the high boiling ether drops to the lower portion of the column.

The bulk type liquid phase reactions of the prior art had as one problem the control of the temperature. The distillation avoids this problem entirely.

The streams containing the olefins to be etherified may be substantially pure olefin streams, such as isobutene or isoamylene. As noted above, it would be desirable to have non-reactive diluents added in order to control the reaction.

The principal current application of the present process of etherification is contemplated for the various $C_4$ and $C_5$ refinery streams, which will contain widely varying concentrations of normal olefins, isoolefins, normal alkanes and isoalkanes. Usually a $C_4$ stream is principally $C_4$ although there may be small amounts of residual $C_3$ and $C_5$ hydrocarbons, usually less than 10 mole %, and similarly the $C_5$ stream may contain correspondingly small amounts of residual $C_4$ and $C_6$ hydrocarbons.

One of the advantages of the present process is that it is effective to remove even very small amounts of olefins, particularly the isoolefins from the feed streams. Economics and the volumes handled would be the limiting considerations where small amounts, e.g., less than 5 mole % of olefin were present in the stream. A further advantage is the separation of isoolefins from normal olefins.

It has been found that a distillation column packed with a properly supported acid catalyst into which the mixed $C_4$ stream and methanol are fed can produce a bottom stream containing methyl tertiary butyl ether and an overhead stream that is relatively free of isobutene.

The alcohols employed are methanol and ethanol. The alcohols may be used alone or in mixtures of any proportion to produce highly complex ether products having unique properties as octane improvers for gasoline.

The olefin feed and the alcohol may be fed into the reaction zone separately or premixed and fed therein in a single stream. Preferably they are fed separately.

The success of the catalytic distillation approach lies in an understanding of the principles associated with distillation. First, because the reaction is occurring concurrently with distillation, the initial reaction product, e.g., methyl tertiary butyl ether, is removed from the reaction zone as quickly as it is formed. This removal of the ether minimizes decomposition of the ether and chaining to form isobutene polymer. Second, because all the $C_4$ or $C_5$ components are boiling, the temperature of the reaction is controlled by the boiling point of the $C_4$ or $C_5$ mixture at the system pressure. The heat of reaction simply creates more boil up, but no increase in temperature. Third, the reaction has an increased driving force because the reaction products have been removed and can not contribute to a reverse reaction (LeChatelier's Principle).

As a result, a great deal of control over the rate of reaction and distribution of products can be achieved by regulating the system pressure. Also, adjusting the through-put (residence time = liquid hourly space velocity$^{-1}$) gives further control of product distribution and degree of isobutene or isoamylene.

The temperature in the reactor is determined by the boiling point of the liquid mixture present at any given pressure, or in the case of any mixture of $C_4$'s or $C_5$'s with alcohol, the boiling point of the unreacted hydrocarbons. The temperature in the lower portions of the column will reflect the constitution of the material in that part of the column, which will be higher than the overhead; that is, at constant pressure a change in the temperature of the system indicates a change in the composition in the column. To change the temperature the pressure is changed. Temperature control in the reaction zone is thus controlled by the pressure; by increasing the pressure, the temperature in the system is increased, and vice versa.

The reaction of olefins, e.g., isobutene with alcohol, e.g., methanol is equilibrium limited; however, by carrying out the reaction in a distillation column reactor and fractionating the formed product, e.g., methyl tertiary butyl ether (MTBE), downward away from the reaction zone, the equilibrium is constantly disrupted and hence the reaction never comes to equilibrium. This has the advantage, of course, of potentially achieving an effective 100% conversion, provided the catalyst bed is of sufficient length such that none of the olefin, e.g., isobutene escapes therefrom to go overhead with the unreacted material, n-butenes. The adjustment of the size of the catalyst bed is an economic consideration to be determined for each reactor and in accordance with the reaction conditions.

The ether system (e.g., MTBE) would normally be considered anhydrous; however, small amounts of water often saturate the feed stream and represent about 400 to 600 ppm thereof. The process will continue to operate in the same fashion, in the presence of this amount of water. Generally the system will be employed with less than 1 mole % water in the feed which will appear as the corresponding tertiary alcohol. Higher concentrations of water will retard the etherification and appear in the distillate.

The hydrocarbon feed to the distillation column reactor is preferably introduced near the lower end of the catalyst bed for the ether reaction, more preferably into the catalyst; and the alcohol is preferably fed at the upper end of the catalyst bed, to allow immediate contact of the isobutene and methanol with the catalyst.

A reflux is preferably included in the system. The reflux ratio could vary over the rate of 0.5 to 20:1. In practice, the higher ratio may be used to compensate for a short catalyst bed such as required for experimental work. In commercial size units the catalyst bed would be provided so that lower reflux and hence higher unit productivity could be obtained at lower operating cost.

Catalysts suitable for the new ether process are cation exchangers, which contain sulfonic acid groups, and which have been obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl chlorobenzene and vinyl xylene. A large variety of methods may be used for preparing these polymers; for example, polymerization alone or in admixture with other monovinyl compounds, or by crosslinking with polyvinyl compounds; for example, with divinyl benzene, divinyl toluene, divinylphenylether and others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric acid or chlorosulfonic acid, or by copolymerizing aromatic compounds which contain sulfonic acid groups (see e.g., U.S. Pat. No. 2,366,007). Further sulfonic acid groups may be introduced into these polymers which already contain sulfonic acid groups; for example, by treatment with fuming sulfuric acid, i.e., sulfuric acid which contains sulfur trioxide. The treatment with fuming sulfuric acid is preferably carried out at 0° to 150° C. and the sulfuric acid should contain sufficient sulfur trioxide after the reaction. The resulting products preferably contain an average of 1.3 to 1.8 sulfonic acid groups per aromatic nucleus. Particulaly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent Specification No. 908,247).

The ion exchange resin is preferably used in a granular size of about 0.25 to 1 mm, although particles from 0.15 mm up to about 1 mm may be employed. The finer catalysts provide high surface area, but also result in high pressure drops through the reactor. The macroreticular form of these catalysts is preferred because of the much larger surface area exposed and the limited swelling which all of these resins undergo in a non-aqueous hydrocarbon medium.

Similarly, other acid resins are suitable, such as perfluorosulfonic acid resins which are copolymers of sulfonyl fluorovinyl ethyl and fluorocarbon and described in greater detail in DuPont "Innovation", Volume 4, No. 3, Spring 1973 or the modified forms thereof as described in U.S. Pat. Nos. 3,784,399; 3,770,567 and 3,849,243.

In addition to pockets of resin catalyst described, catalyst structures described in commonly owned U.S. Pat. No. 4,250,052 and copending U.S. patent application, Ser. No. 307,120, filed Sept. 30, 1981 which are incorporated herein, may be employed.

The present improved etherification process can be briefly described in regard to the figure. This embodiment shows both zones in a single catalytic distillation reactor 10. Zone 11 is the upper zone which is a simple distillation column which would normally have conventional trays (not shown). Zone 11 is separated from the catalytic distillation zone 12 by a header 20 which has a back pressure control valve 21. Below the catalyst section 13 is another conventional distillation section 14, which is part of zone 12.

The hydrocarbon feed, for example a $C_4$ refinery stream having a typical 15 weight % isobutene, enters the reactor 10 via line 30 in the lower end catalyst bed 13. Simultaneously alcohol in this case methanol is fed through line 23 into the upper end of the catalyst bed 13.

The catalyst bed is that described in U.S. Pat. Nos. 4,215,015 and 4,302,356 and consists of fiber glass belts having vertical pockets therein containing Amberlyst 15 (Rohm and Haas) acidic cation exchange resin beads therein with each belt formed into a spiral by wrapping it around stainless steel demister wire. Thus, the catalyst bed is also a distillation structure.

The isobutene is preferentially reacted with the methanol at a pressure of 150 psig. The ether product is fractionated in the catalyst packing and also therebelow in section 14, such that the methyl tertiary butyl ether product withdraw via line 16 is substantially free of methanol. A reboiler 15 recycles a portion of the ether product through line 17 and 18.

The upper zone 11 was operated at several pressures and an overhead 19 recovered from the column. At an upper zone pressure of 150 psig the two zones were operated at a single zone. At upper zone pressures of 70 psig and 20 psig, reduced methanol in the overhead was obtained. The condensate in upper zone 11 was collected at header 20 and returned by pump 22 via lines 24 and 23 to the top of the catalyst bed in zone 12 conveniently into alcohol feed 23. The overhead 19 containing the unreacted $C_4$ stream and azeotroped methanol was condensed in condenser 26 with a portion returned via line 29 as reflux and the remaining portion sent to an alcohol removal section 27. The specific nature of the alcohol removal section 27 is not a part of the present invention. It would appear from current commercial operations that water washing is the method of choice. The removal of alcohol from hydrocarbons by water washing is conventional, and briefly comprises a tower with a counter flow of condensed hydrocarbon and wash water. Steam is used to distill methanol away from the water. In any event, whatever method is used for alcohol removal from the hydrocarbon overhead will require less energy if less alcohol is present. The steam required in the water wash section was also recorded for each level of methanol in the overhead. The results of the operation of upper zone 11 at the different pressures is reported in the TABLE below:

| Pressure in Zone 11, psig | 150 | 70 | 20 |
|---|---|---|---|
| wt. % methanol in overhead 19 | 6.5 | 3.0 | 1-2 |

-continued

| | | | |
|---|---|---|---|
| Condensing Temperature, °F. | 165 | 115 | 60 |
| Steam required for catalytic distillation Column 12, lbs/lb MTBE* | 1.1 | 1.0 | 1.0 |
| Steam required for methanol recovery Column, lb/lb MTBE** | .8 | .3 | .1 |
| Total Steam required | 1.9 | 1.3 | 1.1 |

*0.5:1 reflux ratio
**3:1 reflux ratio

The $C_4$ hydrocarbon feed 22 had the following analysis:

| Mixed $C_4$ Analysis Component | wt. % |
|---|---|
| methane | .03 |
| ethane | .05 |
| propane | .14 |
| propylene | .09 |
| i-butane | 22.02 |
| n-butane | 20.21 |
| butene-1 | 9.27 |
| i-butylene | 16.98 |
| t-butene-2 | 18.86 |
| c-butene-2 | 12.31 |
| pentanes | .04 |
| total | 100.00 |

Figure 2:
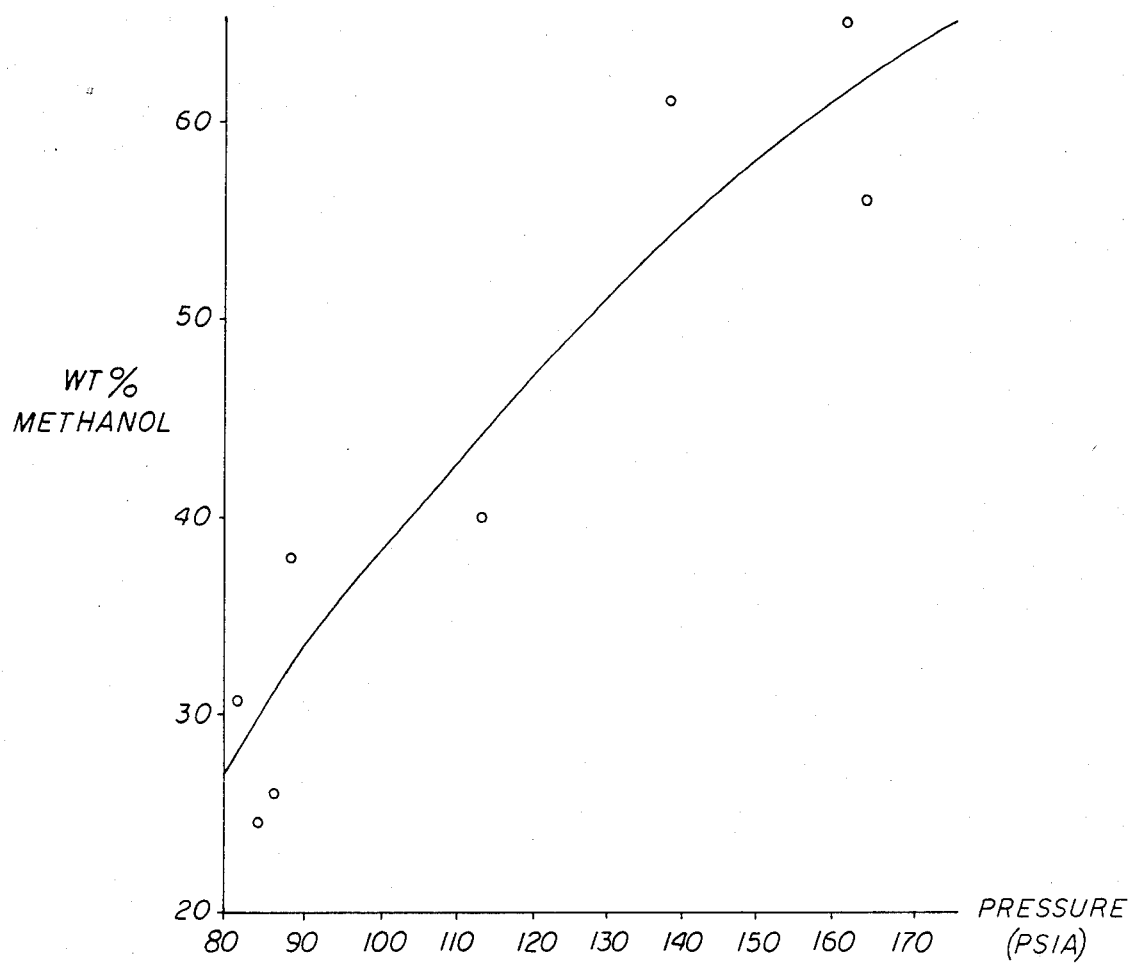
FIG. 2 is a graph showing the change in the composition of the azeotrope as a function of pressure for a $C_4$ system.
Figure 3:
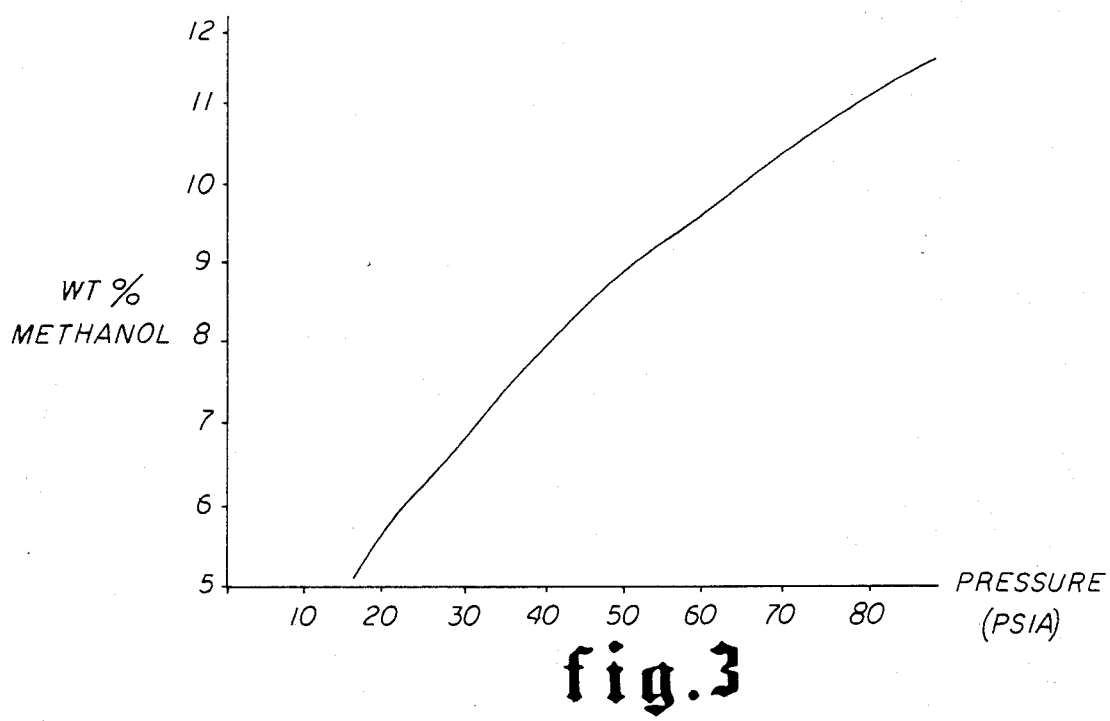
FIG. 3 is a graph showing the change in the composition of the azeotrope as a function of pressure for a $C_5$ system.

The system was used over a range of pressures and the weight percent of methanol in the overhead recorded. This information is reported below in tabular form and depicted in FIG. 2 in graphic form. The same information has been calculated for an isopentane-methanol azeotrope and is shown in FIG. 3.

| AZEOTROPE DATA | | |
|---|---|---|
| Pressure PSIA | Temperature °F. | MeOH wt % |
| System: Mixed $C_4$'s, Methanol (Experimental) | | |
| 81 | 108 | 3.1 |
| 84 | 117 | 2.5 |
| 86 | 112 | 2.6 |
| 89 | 142 | 3.8 |
| 114 | 152 | 4.0 |
| 138 | 160 | 6.1 |
| 161 | 162 | 6.5 |
| 164 | 164 | 5.6 |
| System: Isopentane, Methanol (Calculated by Unifac Equation) | | |
| 20 | 92 | 5.6 |
| 40 | 131 | 7.8 |
| 80 | 173 | 11.1 |

The invention claimed is:

1. A method for producing $C_1$ or $C_2$ alkyl tertiary $C_4$ ether comprising:
   (a) feeding:
      (1) a $C_4$ hydrocarbon stream containing isobutene, and
      (2) an alcohol selected from methanol or ethanol, to a first zone of a distillation column reactor having two separated zones independently operated at different pressures, said first zone containing a fixed bed acidic cation exchange resin,
   (b) concurrently:
      (1) contacting said $C_4$ hydrocarbon stream and said alcohol with said fixed bed acidic cation exchange resin packing in said first zone at a pressure in the range of 140 to 185 psig, thereby catalytically reacting isobutene with said alcohol to form $C_1$ or $C_2$ tertiary $C_4$ ether, and;

(2) distilling the resulting mixture comprising said ether and unreacted materials in said first zone, (3) removing from said first zone a first overhead fraction comprising principally unreacted $C_4$ hydrocarbons and containing minor amounts of ether and alcohol as an azeotrope into a second zone, said second zone being a distillation zone operated at a pressure in the range of 0 to 100 psig thereby producing a second overhead having a reduced amount of alcohol therein from said first overhead, condensing a portion of said first overhead, said condensed portion containing substantially all of said ether and a portion of said alcohol of said first overhead and returning said condensed portion to said first zone, (4) withdrawing said second overhead from said second zone and, (5) withdrawing an ether product substantially free of alcohol from the bottom of said first zone.

2. The method according to claim 1 wherein the pressure in the second zone is in the range of 65 to 85 psig.

3. The method according to claim 1 wherein the pressure in the first zone is in the range of 150 to 180 psig.

4. The method according to claim 3 wherein the pressure in the second zone is in the range of 70 to 75 psig.

5. The method according to claim 1 or 4 wherein alcohol is methanol.

6. The method according to claim 1 or 4 wherein the alcohol is ethanol.

7. The method according to claim 1 wherein said second overhead is condensed and further treated to remove alcohol therefrom.

8. A method of producing $C_1$ or $C_2$ alkyl tertiary $C_5$ ether comprising:

(a) feeding:

(1) a $C_5$ hydrocarbon stream containing isoamylene, and, (2) an alcohol selected from methanol or ethanol, to a first zone of a distillation column reactor having two separated zones independently operated at different pressures, said first zone containing a fixed bed acidic cation exchange resin, (b) concurrently:

(1) contacting said $C_5$ hydrocarbon stream and said alcohol with said fixed bed acidic cation exchange resin packing in said first zone at a pressure in the range of 30 to 70 psig, thereby catalytically reacting isoamylene with said alcohol to form $C_1$ to $C_2$ tertiary $C_5$ ether, and;

(2) distilling the resulting mixture comprising said ether and unreacted materials in said first zone, (3) removing from said first zone a first overhead fraction comprising principally unreacted $C_5$ hydrocarbons and containing minor amounts of ether and alcohol as an azeotrope into a second zone, said second zone being a distillation zone operated at a pressure in the range of 0 to 15 psig thereby producing a second overhead having a reduced amount of alcohol therein from said first overhead, condensing a portion of said first overhead, said condensed portion containing substantially all of said ether and a portion of said alcohol of said first overhead and returning said condensed portion to said first zone, (4) withdrawing said second overhead from said second zone, and (5) withdrawing an ether product substantially free of alcohol from the bottom of said first zone.

9. The method according to claim 8 wherein the pressure in the second zone is in the range of 5 to 15 psig.

10. The method according to claim 11 wherein the pressure in the second zone is in the range of 10 to 15 psig.

11. The method according to claim 8 or 10 wherein alcohol is methanol.

12. The method according to claim 8 or 10 wherein the alcohol is ethanol.

13. The method according to claim 11 wherein said second overhead is condensed and further treated to remove alcohol therefrom.

* * * * *